(12) United States Patent
Ramón

(10) Patent No.: US 7,910,811 B2
(45) Date of Patent: Mar. 22, 2011

(54) TOMATO HYBRID BS 01031842

(75) Inventor: Germán Anastasio Ramón, Murcia (ES)

(73) Assignee: Seminis Vegetable Seeds, Inc., Woodland, CA (US)

( * ) Notice: Subject to any disclaimer, the term of this patent is extended or adjusted under 35 U.S.C. 154(b) by 0 days.

(21) Appl. No.: 12/419,106

(22) Filed: Apr. 6, 2009

(65) Prior Publication Data

US 2009/0255010 A1    Oct. 8, 2009

Related U.S. Application Data

(60) Provisional application No. 61/042,667, filed on Apr. 4, 2008.

(51) Int. Cl.
 *A01H 1/00* (2006.01)
 *C07H 21/04* (2006.01)
 *C07K 14/415* (2006.01)
 *C12N 15/00* (2006.01)

(52) U.S. Cl. ............... 800/317.4; 435/468; 435/411; 435/418; 435/419; 530/370; 536/23.1; 536/23.6; 800/260; 800/278; 800/300; 800/301; 800/302

(58) Field of Classification Search ............... 435/411, 435/468; 530/370; 536/23.6; 800/317.4; Plt./261; 426/106, 615
See application file for complete search history.

(56) References Cited

U.S. PATENT DOCUMENTS

| 6,414,226 B1 * | 7/2002 | Hoogstraten | 800/317.4 |
| 6,787,687 B1 | 9/2004 | Giovannoni et al. | 800/317.4 |

OTHER PUBLICATIONS

Certificate on the Grant of Community Plant Variety Rights, for Tomato Variety (Lycopersicon lycopersicum L. Karsten) FDR152078, dated Dec. 4, 2006, European Union.
Mexican Application for Plant Variety Protection for Tomato Variety (Lycopersicon lycopersicum L. Karsten) FDR 15-2078, dated Jul. 2, 2007.
Mexican Application for Plant Variety Protection for Tomato Variety (Lycopersicon lycopersicum L. Karsten) FDR 15-2078, dated Jul. 2, 2007, (English translation).

* cited by examiner

*Primary Examiner* — Phuong T Bui
(74) *Attorney, Agent, or Firm* — Alissa Eagle, Esq.; SNR Denton US LLP

(57) ABSTRACT

The invention provides seed and plants of the tomato hybrid designated BS 01031842. The invention thus relates to the plants, seeds and tissue cultures of tomato hybrid BS 01031842, and to methods for producing a tomato plant produced by crossing a plant of tomato hybrid BS 01031842 with itself or with another tomato plant, such as a plant of another hybrid. The invention further relates to seeds and plants produced by such crossing. The invention further relates to parts of a plant of tomato hybrid BS 01031842, including the fruit and gametes of such plants.

21 Claims, No Drawings

US 7,910,811 B2

TOMATO HYBRID BS 01031842

This application claims the priority of U.S. Provisional Appl. Ser. No. 61/042,667, filed Apr. 4, 2008, the entire disclosure of which is incorporated herein by reference.

BACKGROUND OF THE INVENTION

1. Field of the Invention

The present invention relates to the field of plant breeding and, more specifically, to the development of tomato hybrid BS 01031842.

2. Description of Related Art

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform lines requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop which has been subject to such breeding programs and is of particular value is the tomato. The common tomato, *Solanum lycopersicum*(formerly *Lycopersicon esculentum* Mill.) is widely cultivated domestically and internationally. Of the approximately 500,000 acres of tomatoes grown annually in the United States, roughly 40% are grown for fresh market consumption, with the balance grown for processing.

Most cultivated tomatoes are diploid, self-fertile and mostly self-pollinating, with hermaphroditic flowers. Tomatoes having different ploidy levels are not uncommon and were already known in the 1920's and 30's (Linstrom, 1940). Prior to the mid-1970's, most commercial cultivars were pure breeding lines. Since then, better performing hybrid cultivars have been replacing the pure breeding lines. Today, most commercial varieties are hybrids. Due to its wide dissemination and high value, the tomato species has been intensively bred, providing a wide variety of lines with different traits. Tomato fruits from different cultivars show tremendous variation in weight and shape. Common groupings in the marketplace include the cherry, plum, pear, standard (or round), and beefsteak types.

While breeding efforts to date have provided a number of useful tomato lines and varieties with beneficial traits, there remains a great need in the art for new lines and hybrids with further improved traits. Such plants would benefit farmers and consumers alike by improving crop yield and/or fruit quality.

SUMMARY OF THE INVENTION

As tomato production becomes increasingly more modernized, there has been a concomitant demand for tomato varieties adapted for production in newer facilities, for example, high-tech glasshouses compared to screenhouses or open fields. Growing cycles under modernized systems are also expanding, and may last 6-10 months. Thus, varieties adapted to modern production that also continuously produce fruit are needed.

Indeterminate growth varieties are adapted to long cropping cycles. Tomatoes grown under the greater protection provided by modern production facilities often produce improved quality fruit, allowing for easier access to export markets. These production facilities are also particularly beneficial when using environmentally friendly systems such as an integrated pest management program. However, to service these markets, a longer post-harvest period is needed in order to satisfy both the consumers and the distribution channels. Additionally, many insects are biological vectors for plant viruses. Exposure can be minimized by high-tech production methods, but are not completely avoidable.

Genetic resistance found naturally in related wild species of tomato, may be introduced into commercial varieties to accomplish crop protection concurrent with environmental friendly production technologies.

The present invention overcomes limitations in the prior art by providing, for example, seeds and plants of a tomato variety having a combination of genes, the expression of which provides a number of advantageous traits, such as an appropriate plant growth habit for protected production, a long post-harvest storage period, high quality and palatability of the fruit which are very large, round, red, and uniform, and resistance to many diseases, specifically insect transmitted diseases such as Tomato Spotted Wilt Virus (TSWV) and Tomato Yellow Leaf Curl Virus (TYLCV).

The invention also carries in its genome Ripening inhibitor (rin), a single recessive natural ripening mutation that has been reported as improving fruit firmness and shelf life when introduced into other tomato varieties in the hetero-hybrid form.

In one aspect, the present invention provides a tomato plant of the hybrid designated BS 01031842. Also provided are tomato plants having all the physiological and morphological characteristics of the tomato hybrid designated BS 01031842. Parts of the tomato plant of the present invention are also provided, for example, including pollen, an ovule, a fruit, a scion, a rootstock and a cell of the plant.

The invention also concerns the seed of tomato hybrid BS 01031842. The tomato seed of the invention may be provided as an essentially homogeneous population of tomato seed of the hybrid designated BS 01031842. Essentially homogeneous populations of seed are generally free from substantial numbers of other seed. Therefore, seed of hybrid BS 01031842 may be defined as forming at least about 97% of the total seed, including at least about 98%, 99% or more of the seed. The seed population may be separately grown to provide an essentially homogeneous population of tomato plants designated BS 01031842.

In another aspect of the invention, a plant of tomato hybrid BS 01031842 comprising an added heritable trait is provided. The heritable trait may comprise a genetic locus that is, for example, a dominant or recessive allele. In one embodiment of the invention, a plant of tomato hybrid BS 01031842 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of tomato hybrid BS 01031842 is provided. The tissue culture will preferably be capable of regenerating plants capable of expressing all of the physiological and morphological characteristics of the hybrid, and of regenerating plants having substantially the same genotype as other plants of the hybrid. Examples of some of the physiological and morphological characteristics of the hybrid BS 01031842 include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides tomato plants regenerated from a tissue culture of the invention, the plants having all the physiological and morphological characteristics of hybrid BS 01031842.

In yet another aspect of the invention, processes are provided for producing tomato seeds, plants and fruit, which processes generally comprise crossing a first parent tomato plant with a second parent tomato plant, wherein at the first and second parent tomato plants are the parent plants of the hybrid designated BS 01031842. These processes may be further exemplified as processes for preparing hybrid tomato seed or plants, wherein a first tomato plant is crossed with a second tomato plant of a different, distinct line to provide a tomato plant of the hybrid variety BS 01031842. In these processes, crossing will result in the production of seed. The seed production occurs regardless of whether the seed is collected or not.

Where a plant is self-pollinated, pollination may occur without the need for direct human intervention other than plant cultivation. In one embodiment of the invention, the first step in "crossing" comprises planting seeds of a first and second parent tomato plant, often in proximity so that pollination will occur for example, mediated by insect vectors. Alternatively, pollen can be transferred manually.

A second step may comprise cultivating or growing the seeds of first and second parent tomato plants into plants that bear flowers. A third step may comprise preventing self-pollination of the plants, such as by emasculating the male portions of flowers, (e.g., treating or manipulating the flowers to produce an emasculated parent tomato plant). Self-incompatibility systems may also be used in some hybrid crops for the same purpose. Self-incompatible plants still shed viable pollen and can pollinate plants of other varieties but are incapable of pollinating themselves or other plants of the same hybrid.

A fourth step for a hybrid cross may comprise cross-pollination between the first and second parent tomato plants. In certain embodiments, pollen may be transferred manually or by the use of insect vectors. Yet another step comprises harvesting the seeds from at least one of the parent tomato plants. The harvested seed can be grown to produce a tomato plant or hybrid tomato plant.

The invention also concerns methods of vegetatively propagating a plant of tomato hybrid BS 01031842. In certain embodiments, the method comprises the steps of: (a) collecting tissue capable of being propagated from a plant of tomato hybrid BS 01031842; (b) cultivating said tissue to obtain proliferated shoots; and (c) rooting said proliferated shoots to obtain rooted plantlets. In some of these embodiments, the method further comprises growing plants from said rooted plantlets.

In another aspect of the invention, a plant of tomato hybrid BS 01031842 comprising an added heritable trait is provided. The heritable trait may comprise a genetic locus that is, for example, a dominant or recessive allele. In one embodiment of the invention, a plant of tomato hybrid BS 01031842 is defined as comprising a single locus conversion. For example, one or more heritable traits may be introgressed at any particular locus using a different allele that confers the new trait or traits of interest. In specific embodiments of the invention, the single locus conversion confers one or more traits such as, for example, herbicide tolerance, insect resistance, disease resistance and modulation of plant metabolism and metabolite profiles. In further embodiments, the trait may be conferred by a naturally occurring gene introduced into the genome of the hybrid by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

For example, in certain embodiments, the invention provides methods of introducing a desired trait into tomato hybrid BS 01031842 comprising: (a) crossing a plant of a first parent of hybrid BS 01031842 with a second tomato plant that comprises a desired trait to produce F1 progeny, (b) selecting an F1 progeny that comprises the desired trait, (c) crossing the selected F1 progeny with a plant of the same first parent of hybrid BS 01031842 to produce backcross progeny, (d) selecting backcross progeny comprising the desired trait and the physiological and morphological characteristic of the first parent of tomato hybrid BS 01031842, (e) repeating steps (c) and (d) three or more times in succession to produce selected fourth or higher backcross progeny that comprise the desired trait and all of the physiological and morphological characteristics of the first parent of hybrid BS 01031842 when grown in the same environmental conditions; and (f) crossing a plant produced as described through step (e) above with the other, second parent of hybrid BS 01031842. The invention also provides tomato plants produced by these methods.

In certain embodiments, the present invention provides a method of producing tomatoes comprising: (a) obtaining a plant of tomato hybrid BS 01031842, wherein the plant has been cultivated to maturity, and (b) collecting tomatoes from the plant.

In still yet another aspect of the invention, the genetic complement of the tomato plant hybrid designated BS 01031842 is provided. The phrase "genetic complement" is used to refer to the aggregate of nucleotide sequences, the expression of which defines the phenotype of, in the present case, a tomato plant of, or a cell or tissue of that plant. A genetic complement thus represents the genetic makeup of a cell, tissue or plant, and a hybrid genetic complement represents the genetic make up of a hybrid cell, tissue or plant. The invention thus provides tomato plant cells that have a genetic complement in accordance with the tomato plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that hybrid BS 01031842 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by tomato plant cells, tissues, plants, and seeds, formed by the combination of a haploid genetic complement of a tomato plant of the invention with a haploid genetic complement of a second tomato plant, preferably, another, distinct tomato plant. In another aspect, the present invention provides a tomato plant regenerated from a tissue culture that comprises a hybrid genetic complement of this invention.

In still yet another aspect, the invention provides a method of determining the genotype of a plant of tomato hybrid BS 01031842 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, plant parts, seeds and derivatives of tomato hybrid BS 01031842. This hybrid can be described as having a combination of genes, the expression of which provides a number of advantageous traits, such as a normal, indeterminate, semi-erect growth habit with a medium canopy such that it is appropriate for protected production. Also, tomato hybrid BS 01031842 carries in its genome Ripening inhibitor (rin), and has a long post-harvest storage period. The fruit are high quality and palatable; they are typically very large (about 232 grams), round (about 62 mm long with a 79 mm diameter), and red in color. The invention also exhibits resistance to many diseases, specifically insect transmitted diseases Tomato Spotted Wilt Virus (TSWV) and Tomato Yellow Leaf Curl Virus (TYLCV), but also various races of Tobacco Mosaic Virus (TMV), various races of *Fusarium* wilt, and *Verticillium* wilt. This variety shows uniformity and stability within the limits of environmental influence for the traits described hereinafter.

A. PHYSIOLOGICAL AND MORPHOLOGICAL CHARACTERISTICS OF TOMATO HYBRID BS 01031842

Tomato cultivars may be grouped by maturity, i.e. the time required from planting the seed to the stage where fruit harvest can occur. Standard maturity classifications include 'early', 'midseason' or 'late-maturing'. Another classification for tomatoes is the developmental timing of fruit set. 'Determinant' plants grow foliage, then transition into a reproductive phase of flower setting, pollination and fruit development. Consequently, determinant cultivars have a large proportion of the fruit ripen within a short time frame. Growers that harvest only once in a season favor determinant type cultivars. In contrast, 'indeterminate' types grow foliage, then enter a long phase where flower and fruit development proceed along with new foliar growth. Growers that harvest the same plants multiple times favor indeterminate type cultivars. In response to more recent consumer demands for dietary diversity, tomato breeders have developed a wider range of colors. In addition to expanding the range of red colored fruits, there are cultivars that produce fruits that are creamy white, lime green, yellow, green, golden, orange and purple. Additionally, there are multi-colored varieties exemplified by mainly red fruited lines with green shoulders, and both striped- and variegated-colored fruit. Standard methods for determining tomato fruit color are described, for instance, in Gull et al. (1989) and Kader et al. (1978), both of which are incorporated by reference herein.

In accordance with one aspect of the present invention, there is provided a plant having the physiological and morphological characteristics of tomato hybrid BS 01031842. A description of the physiological and morphological characteristics of tomato hybrid BS 01031842 is presented in Table 1.

TABLE 1

| Physiological and Morphological Characteristics of Hybrid BS 01031842 | |
|---|---|
| CHARACTERISTIC | BS 01031842 |
| 1. Seedling | |
| Anthocyanin in Hypocotyl of 2-15 cm Seeding | Present |
| Habit of 3-4 Weeks Old Seeding | Normal |
| 2. Mature Plant | |
| Height | 234 cm |
| Growth | Indeterminate |
| Form | Normal |
| Size of Canopy (compared to others of similar type) | Medium |
| Habit | Semi-Erect |
| 3. Stem | |
| Branching | sparse |
| Branching at Cotyledonary of First Leafy Node | Absent |
| No. of Nodes Between First Inflorescence: | 5 |
| No. of Nodes between Early Inflorescences | 4 |
| No. of Nodes Between Later Developing Inflorescences | 3 |
| Pubescence on Younger Stems | Sparsely Hairy |
| 4. Leaf | |
| Type | Tomato |
| Margins of Major Leaflets | Nearly Entire |
| Marginal Rolling or Wiltiness | Slight |
| Onset of Leaflet Rolling | Late Season |
| Surface of Major Leaflets | Rugose (Bumpy or Veiny) |
| Pubescence | Normal |
| 5. Inflorescence | |
| Type | Simple |
| Number of Flowers in Inflorescence | Average - 6 |
| Leafy or Running Inflorescences | Occasional |
| 6. Flower | |
| Calyx | Normal, Lobes Awl-Shaped |
| Calyx Lobes | Shortly than Corolla |
| Corolla Color | Yellow |
| Style Pubescence | Sparse |
| Anthers | All Fused into Tube |
| Fasciation | Occasionally Present |
| 7. Fruit | |
| Typical Fruit Shape | |
| Shape of Transverse Section | Angular |
| Shape of Stem End | Indented |
| Shape of Blossom End | Flat |
| Shape of Pistil Scar | Stellate |
| Abscission Layer | Present (Pedicellate) |
| Point of Detachment of Fruit at Harvest | At Pedicel Joint |
| Length of Dedicel (from joint to calyx attachment) | 13 mm |
| Length of Mature Fruit (stem axis) | 62 mm |
| Diameter of Fruit at Widest Point | 79 mm |
| Weight of Mature Fruit | 232 g |
| No. of Locules | Five or More |
| Fruit Surface | Slightly Rough |
| Fruit Base Color (mature-green stage) | Apple or Medium Green (Heinz 1439 VF) |
| Fruit Pattern (mature-green stage) | Uniform Green |
| Shoulder Color if Different from Base | No |
| Fruit Color, Full-Ripe | Red |
| Flesh Color, Full-Ripe | Red/Crimson |
| Flesh Color | With Lighter and Darker Areas in Walls |
| Locular Gel Color of Table-Ripe | Red |
| Ripening | Uniform |
| Ripening | Uniformly |
| Stem Scar Size | Medium (Rutgers) |
| Core | Present |
| Epidermis Color | Yellow |
| Epidermis | Normal |
| Epidermis Texture | Average |
| Anthocyanin in Hypocotyl of 2-15 mc Seedling | Present |

TABLE 1-continued

Physiological and Morphological Characteristics of Hybrid BS 01031842

| CHARACTERISTIC | BS 01031842 |
|---|---|
| 8. Resistance to Fruit Disorder | |
| Blotchy Ripening | Resistant |
| Bursting | Resistant |
| Catface | Resistant |
| Cracking Concentric | Resistant |
| Cracking, radial | Resistant |
| Gold Fleck | Resistant |
| Graywall | Resistant |
| Zippering | Resistant |
| 9. Disease and Prest Reaction | |
| Viral Diseases: | |
| Blotchy Ripening | Resistant |
| Tobacco Mosaic, Race 0 | Resistant |
| Tobacco Mosaic, Race 1 | Resistant |
| Tobacco Mosaic, Race 2 | Resistant |
| Cracking, Concentric | Resistant |
| Tomato Spotted Wilt | Resistant |
| Other Virus (TYLCV) | Resistant |
| Fungal Diseases: | |
| Collar Rot or Stem Canker (*Alternaria solani*) | Resistant |
| *Fusarium* Wilt, Race 1 (*F. oxysporum f. lycopersici*) | Resistant |
| *Fusarium* Wilt, Race 2 | Resistant |
| *Fusarium* Wilt, race 3 | Susceptible |
| *Verticillium* Wilt, Race 1 (*V. albo-atrum*) | Resistant |
| 10. Chemistry and Composition of Full-Ripe Fruits | |
| Titratable Acidity, as % Citric | 0.35 |
| Soluble Solids as Brix | 6.0 |
| 11. Phenology | |
| Fruiting Season | Long (Marglobe) |
| Relative Maturity in Areas Tested | Medium |
| 12. Adaptation | |
| Culture | Greenhouse |
| Principle Use | Fresh Market |
| Machine Harvest | Not Adapted |

*These are typical values. Values may vary due to environment. Other values that are substantially equivalent are also within the scope of the invention.

As shown in Table 1 above, hybrid BS 01031842 typically has an indeterminate growth pattern, a medium canopy, and a normal, habit. The stem is usually sparsely branched and sparsely hairy. The leaves usually have entire margins with slight rolling late in the season, and are rugose. The inflorescence is typically simple with 6 yellow flowers. The anthers are usually fused, and the calyx normal and awl-shaped. The mature fruit is usually about 62 mm long, with a diameter of about 79 mm, and a weight of about 232 grams. The fruit is typically a uniform medium to apple green at the mature-green stage, and red when fully ripe with red to crimson flesh. The fruit soluble solids (as Brix) is usually about 6, and the titratable acidity about 0.35

B. BREEDING TOMATO HYBRID BS 01031842

One aspect of the current invention concerns methods for crossing the tomato hybrid BS 01031842 with itself or a second plant and the seeds and plants produced by such methods. Further hybrid seeds are produced by crossing hybrid BS 01031842 with second tomato parent line or variety.

The development of new varieties using one or more starting varieties is well known in the art. In accordance with the invention, novel varieties may be created by crossing hybrid BS 01031842 followed by multiple generations of breeding according to such well known methods. New varieties may be created by crossing with any second plant. In selecting such a second plant to cross for the purpose of developing novel lines, it may be desired to choose those plants that either themselves exhibit one or more selected desirable characteristics or that exhibit the desired characteristic(s) when in hybrid combination. Once initial crosses have been made, inbreeding and selection take place to produce new varieties. For development of a uniform hybrid, often five or more generations of selfing and selection are involved.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with hybrid BS 01031842 and progeny thereof to achieve a homozygous derivative variety.

Backcrossing can also be used to improve an inbred plant. Backcrossing transfers one or more specific, desirable traits from one inbred or non-inbred source to an inbred that lacks those traits. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous at loci controlling the characteristic being transferred, but are like the superior parent for most or almost all other loci. The last backcross generation would be selfed to give pure breeding progeny for the trait being transferred.

The parental tomato plant which contributes the desired characteristic or characteristics is termed the non-recurrent parent because it can be used one time in the backcross protocol and therefore need not recur. The parental tomato plant to which the locus or loci from the non-recurrent parent are transferred is known as the recurrent parent as it is used for several rounds in the backcrossing protocol.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection or screening may be applied where the single locus (e.g. allele) acts in a dominant fashion. For example, when selecting for a dominant allele providing resistance to a bacterial disease, the progeny of the initial cross can be inoculated with bacteria prior to the backcrossing. The inoculation then eliminates those plants which do not have the resistance, and only those plants which have the resistance allele are used in the subsequent backcross. This process is then repeated for all additional backcross generations.

Selection of tomato plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay that is able to identify the relative presence or absence of a trait of interest in a plant can also be useful for breeding purposes. Procedures for marker assisted selection applicable to the breeding of tomato are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Simple Sequence Repeats (SSR), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

Tomato varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Methods for increasing the ploidy level of a diploid plant are also well known in the art. For example, by treating cells of a diploid plant with colchicine, tetraploid plants may be retrieved. Triploids may be formed, for example, by fertilizing a doubled-haploid ovule with haploid pollen. Other techniques for manipulating ploidy levels include somatic hybridization or protoplast fusion. Any of such techniques may be used in accordance with the invention.

Tomatoes can be grown for use as rootstocks or scions. Typically, different types of tomatoes are grafted to enhance disease resistance, which is usually conferred by the rootstock, while retaining the horticultural qualities usually conferred by the scion. It is not uncommon for grafting to occur between *Solanum lycopersicum* lines and related *Solanum* species. Methods of grafting and vegetative propagation are well-known in the art.

C. PERFORMANCE CHARACTERISTICS

As described above, hybrid BS 01031842 exhibits desirable agronomic traits, including an appropriate plant growth habit for protected production, a long post-harvest storage period, high quality and palatability of the fruit which are very large, round, red, and uniform, and resistance to many diseases, specifically insect transmitted diseases such as Tomato Spotted Wilt Virus (TSWV) and Tomato Yellow Leaf Curl Virus (TYLCV).

D. PLANTS DERIVED FROM TOMATO HYBRID BS 01031842 BY GENETIC ENGINEERING

Many useful traits that can be introduced by backcrossing, as well as directly into a plant, are those that are introduced by genetic transformation techniques. Genetic transformation may therefore be used to insert a selected transgene into the tomato hybrid of the invention or may, alternatively, be used for the preparation of transgenes that can introduced by backcrossing. Methods for the transformation of plants, including tomato, are well known to those of skill in the art. Techniques which may be employed for the genetic transformation of tomato include, but are not limited to, electroporation, microprojectile bombardment, *Agrobacterium*-mediated transformation, pollen-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

To effect pollen-mediated transformation, one may apply pollen pretreated with DNA to the female reproduction parts of tomato plants for pollination. A pollen-mediated method for the transformation of tomato is disclosed in U.S. Pat. No. 6,806,399.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target tomato cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant species where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for tomato plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly, partially duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the tomato lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a tomato plant according to the invention. Non-limiting examples of particular genes and corresponding phenotypes one may choose to introduce into a tomato plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (e.g., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

E. DEFINITIONS

In the description and tables herein, a number of terms are used. In order to provide a clear and consistent understanding of the specification and claims, the following definitions are provided:

Alleles: Alternate forms of a single gene.

Backcrossing: A process in which a breeder repeatedly crosses hybrid progeny, for example a first generation hybrid ($F_1$), back to one of the parents of the hybrid progeny. Backcrossing can be used to transfer genetic information (e.g., an allele) from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Locus: A designated location on a chromosome.

Marker: A readily detectable phenotype, preferably inherited in codominant fashion (both alleles at a locus in a diploid heterozygote are readily detectable), with no environmental variance component, i.e., a heritability of 1.

Polyploid: A cell or organism of containing three or more complete sets of chromosomes.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits whose phenotypes are usually continuously distributed.

Regeneration: The development of a plant from tissue culture.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Self-pollination: The transfer of pollen from the anther to the stigma of the same plant.

Single Locus Converted (Conversion) Plant: A plant, often developed through the backcrossing technique, having essentially all of the desired morphological and physiological characteristics of given variety, expect that at one locus it contains the genetic material (e.g., an allele) from a different variety. Genetic transformation may also be used to develop single locus converted plants.

Substantially Equivalent: A characteristic that, when compared, does not show a statistically significant difference (e.g., $p=0.05$) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a tomato plant by transformation.

Triploid: A cell or organism having three sets of chromosomes.

F. DEPOSIT INFORMATION

A deposit of tomato hybrid BS 01031842, disclosed above and recited in the claims, has been made with the American Type Culture Collection (ATCC), 10801 University Blvd., Manassas, Va. 20110-2209. The date of deposit was Aug. 13, 2007. The accession number for those deposited seeds of tomato hybrid BS 01031842 is ATCC Accession No. PTA-8594. Upon issuance of a patent, all restrictions upon the deposit will be removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275

U.S. Pat. No. 5,378,619
U.S. Pat. No. 6,806,399
WO 99/31248
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Gull et al., *J. Amer. Soc. Hort. Sci.* 114:950-954, 1989.
Kader et al. *Hort. Sci.*, 13:577-578, 1978.
Klee et al., *Bio-Technology*, 3(7):637-642, 1985.
Kopecky et al., *Crop Science*, 45:274-281, 2005.
Kuhlemeier et al., *Plant Cell*, 1:471, 1989.
Linstrom, *Genetics*, 26:387-397, 1940.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 18:6531-6535, 1990.

What is claimed is:

1. A seed of tomato hybrid BS 01031842, a sample of seed of said hybrid having been deposited under ATCC Accession Number PTA-8594.

2. A plant grown from the seed of claim 1.

3. A plant part of the plant of claim 2.

4. The plant part of claim 3, wherein said part is selected from the group consisting of a fruit, a rootstock, a scion, a cell, an ovule and pollen.

5. A tomato plant, or a part thereof, having all the physiological and morphological characteristics of the tomato plant of claim 2.

6. A tissue culture of regenerable cells of tomato hybrid BS 01031842, a sample of seed of said hybrid having been deposited under ATCC Accession Number PTA-8594.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A tomato plant regenerated from the tissue culture of claim 6, wherein the regenerated plant expresses all of the physiological and morphological characteristics of tomato hybrid BS 01031842, a sample of seed of said hybrid having been deposited under ATCC Accession Number PTA-8594.

9. A method of producing tomato seed, comprising crossing the plant of claim 2 with itself or a second tomato plant.

10. The method of claim 9, wherein said second tomato plant is diploid.

11. The method of claim 9, wherein said second tomato plant is not a diploid.

12. The method of claim 9, wherein the plant of tomato hybrid BS 01031842 is the female parent.

13. A method for producing a seed of a hybrid BS 01031842-derived tomato plant comprising the steps of:
   (a) selfing or crossing a tomato plant of hybrid BS 01031842, a sample of seed of said hybrid having been deposited under ATCC Accession Number PTA-8594, with a second tomato plant; and
   (b) allowing seed of a BS 01031842-derived tomato plant to form.

14. The method of claim 13, further comprising the steps of:
   (c) selfing or outcrossing the plant grown from said BS 01031842-derived tomato seed to yield additional BS 01031842-derived tomato seed;
   (d) growing said additional BS 01031842-derived tomato seed of step (c) to yield additional BS 01031842-derived tomato plants; and
   (e) repeating the steps of (c) and (d) to generate further BS 01031842-derived tomato plants.

15. A method of vegetatively propagating a plant of tomato hybrid BS 01031842 comprising the steps of:
   (a) collecting tissue capable of being propagated from a plant of tomato hybrid BS 01031842, a sample of seed of said hybrid having been deposited under ATCC Accession Number PTA-8594;
   (b) cultivating said tissue to obtain proliferated shoots; and
   (c) rooting said proliferated shoots to obtain rooted plantlets.

16. The method of claim 15, further comprising growing plants from said rooted plantlets.

17. A method of introducing a desired trait into a tomato plant comprising:
   (a) crossing a first plant of hybrid BS 01031842, a sample of seed of said hybrid having been deposited under ATCC Accession Number PTA-8594, with a second tomato plant that comprises a desired trait to produce F1 progeny;
   (b) selecting an F1 progeny that comprises the desired trait;
   (c) crossing the selected F1 progeny with said plant of hybrid BS 01031842 or a different plant of hybrid BS 01031842 to produce backcross progeny;
   (d) selecting backcross progeny comprising the desired trait and the physiological and morphological characteristics of tomato hybrid BS 01031842; and
   (e) repeating steps (c) and (d) three or more times in succession to produce selected fourth or higher backcross progeny that comprises the desired trait.

18. A method of producing a plant of tomato hybrid BS 01031842, a sample of seed of said hybrid having been deposited under ATCC Accession Number PTA-8594, comprising an added desired trait, the method comprising introducing a transgene conferring the desired trait into tomato hybrid BS 01031842.

19. A method of determining the genotype of the plant of claim 2 or a first generation progeny thereof, comprising obtaining a sample of nucleic acids from said plant and detecting in said nucleic acids a plurality of polymorphisms, thereby determining the genotype of the plant.

20. The method of claim 19, further comprising the step of storing the results of detecting the plurality of polymorphisms on a computer readable medium.

21. A method of producing tomatoes comprising:
   (a) obtaining the plant of claim 2, wherein the plant has been cultivated to maturity; and
   (b) collecting tomatoes from the plant.

* * * * *